United States Patent [19]

Dürr et al.

[11] Patent Number: 4,824,466
[45] Date of Patent: Apr. 25, 1989

[54] HETEROCYCLYLALKYL ESTERS OF 2-IMIDAZOLINONENICOTINIC ACIDS

[75] Inventors: Dieter Dürr, Bottmingen; Henry Szczepanski, Wallbach, both of Switzerland

[73] Assignee: Ciba-Geigy Corporation, Ardsley, N.Y.

[21] Appl. No.: 166,276

[22] Filed: Mar. 10, 1988

Related U.S. Application Data

[62] Division of Ser. No. 902,805, Sep. 2, 1986, Pat. No. 4,741,763.

[30] Foreign Application Priority Data

Sep. 9, 1985 [CH]  Switzerland ............................ 3881/85
Feb. 27, 1986 [CH]  Switzerland ............................ 780/86

[51] Int. Cl.$^4$ ..................... A01N 43/40; C07D 401/14
[52] U.S. Cl. .................................. 71/92; 71/90; 546/167; 546/278
[58] Field of Search ............... 546/283, 284, 278, 167; 71/92, 90

[56] References Cited

U.S. PATENT DOCUMENTS 4,404,012  9/1983  Orwick et al. ........................... 71/92
4,647,301  3/1987  Los ........................................ 546/278

Primary Examiner—Jane T. Fan
Attorney, Agent, or Firm—Kevin T. Mansfield; Edward McC. Roberts

[57] ABSTRACT

Novel heterocyclylalkyl esters of 2-imidazolinonenicotinic acids of formula I below have good selective herbicidal properties pre- and postemergence and also influence or inhibit plant growth.

The novel esters have the formula I

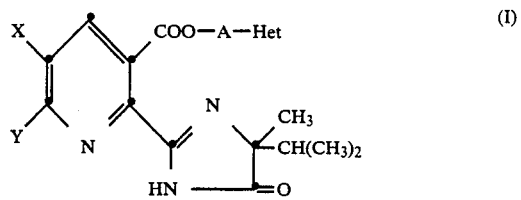

wherein

A is a straight chain or branched $C_1$–$C_4$alkylene bridge,

X and Y are each independently of the other hydrogen, $C_1$–$C_3$alkyl, $C_1$–$C_3$haloalkyl, $C_1$–$C_3$alkoxy, $C_1$–$C_3$haloalkoxy or halogen, or X and Y together form the butadiene bridge, which may be substituted by halogen, cyano or $C_1$–$C_4$alkyl, and Het is a 5- or 6-membered heterocycle which contains one to three nitrogen atoms and/or one oxygen or sulfur atom and which may further contain one or two carbonyl groups, which heterocycle may also be fused to benzene rings and/or substituted by halogen, $C_1$–$C_3$alkyl, $C_1$–$C_3$haloalkyl, $C_1$–$C_3$alkoxy, $C_1$–$C_3$haloalkoxy, nitro, amino, $C_1$–$C_3$alkylamino or di($C_1$–$C_3$)alkylamino.

9 Claims, No Drawings

HETEROCYCLYLALKYL ESTERS OF 2-IMIDAZOLINONENICOTINIC ACIDS

This is a divisional of application Ser. No. 902,805 filed on Sept. 2, 1986 now U.S. Pat. No. 4,741,763 issued May 3, 1988.

The present invention relates to novel herbicidal and plant growth regulating heterocyclylalkyl esters of 2-imidazolinonenicotinic acids, as well as to the preparation of these novel compounds. The invention also relates to compositions containing the novel 2-imidazolinonenicotinic acid esters, and to methods of using them for selectively controlling weeds or for regulating plant growth.

The novel heterocyclylalkyl esters of 2-imidazolinonenicotinic acids have the formula I

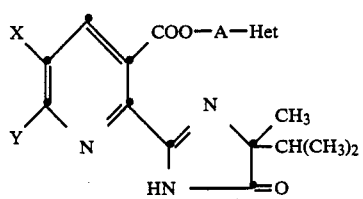
(I)

wherein
A is a straight chain or branched $C_1$-$C_4$alkylene bridge,
X and Y are each independently of the other hydrogen, $C_1$-$C_3$alkyl, $C_1$-$C_3$haloalkyl, $C_1$-$C_3$alkoxy, $C_1$-$C_3$haloalkoxy or halogen, or X and Y together form the butadiene bridge CH=CH—CH=CH, which may be substituted by halogen, cyano or $C_1$-$C_4$alkyl, and
Het is a 5- or 6-membered heterocycle which contains one to three nitrogen atoms and/or one oxygen or sulfur atom and which may further contain one or two carbonyl groups, which heterocycle may also be fused to benzene rings and/or substituted by halogen, $C_1$-$C_3$alkyl, $C_1$-$C_3$haloalkyl, $C_1$-$C_3$alkoxy, $C_1$-$C_3$haloalkoxy, nitro, amino, $C_1$-$C_3$alkylamino or di($C_1$-$C_3$)alkylamino, or Het is the 2-(4,5-dihydro-3-methylthio-6-tert-butyl-1,3,4-triazin-5-on-2-ylhydrazine oxime)furfur-5-yl radical, with the proviso that Het may not be the unsubstituted furyl radical.

In the above definitions, the alkyl and alkylene groups may be straight chain or branched, e.g. methyl, methylene, ethyl, ethylene, propyl, propylene, isopropyl, 1- or 2-methylethylene, butyl, butylene, sec-butyl, 1-methylpropylene, isobutyl, 2-methylpropylene, tert-butyl, 2,2-dimethylethylene and 1,2-dimethylethylene.

Halogen is fluorine, chlorine, bromine or iodine.

The heterocycles defined under Het comprise e.g. pyrrole, pyrrolidine, pyrrolidinone, pyrrolinone, pyrrolinedione, pyridine, pyridinone, pyridinedione, piperidine, piperidinone, imidazole, imidazolinone, pyrazole, pyrazolone, piperazine, diazine, diazinone, piperazinone, triazole, triazolone, triazine, triazinone, benzazole, indole, quinoline, quinolinone, benzodiazole, benzodiazolone, furfuryl, tetrahydrofuran, pyran, oxazole, oxadiazole, morpholine, thiophene, thiazole, thiadiazole and thiomorpholine.

The proviso that Het is not furan is applicable.

These rings may be unsubstituted or substituted by halogen, $C_1$-$C_3$alkyl, $C_1$-$C_3$haloalkyl, $C_1$-$C_3$alkoxy, $C_1$-$C_3$haloalkoxy, nitro, amino, $C_1$-$C_3$alkylamio or di($C_1$-$C_3$)alkylamino.

The preparation of such compounds can be represented by the following scheme:

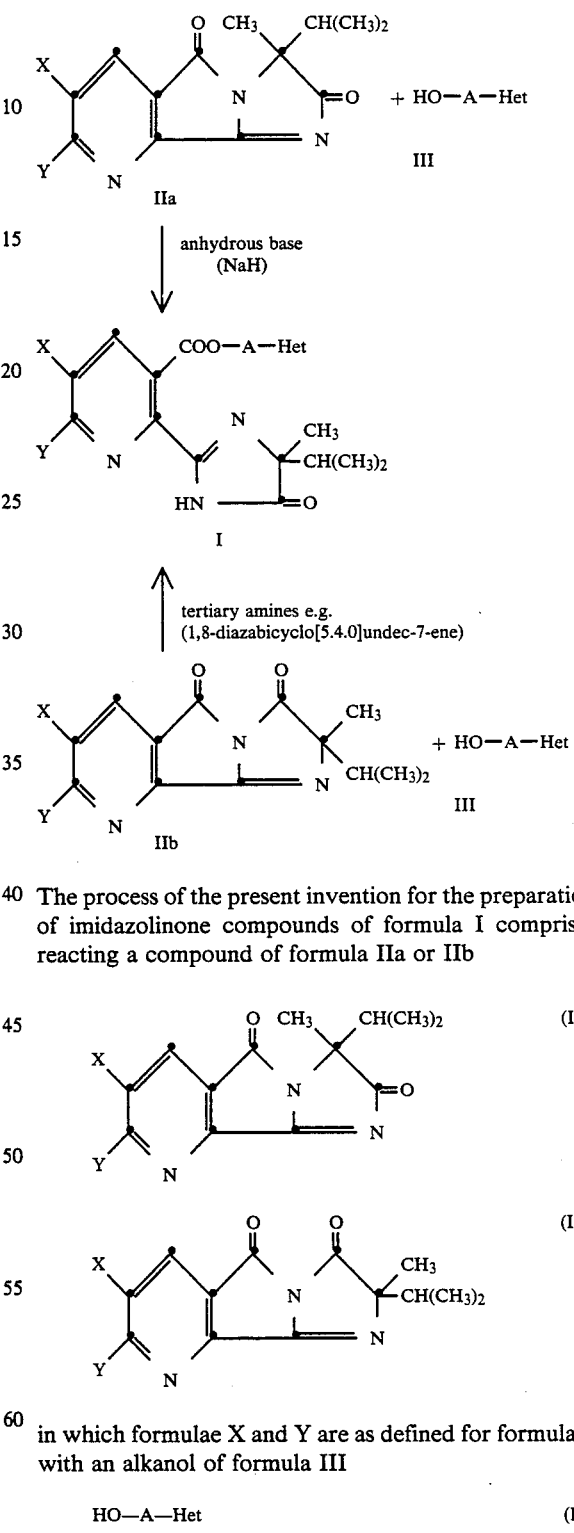

The process of the present invention for the preparation of imidazolinone compounds of formula I comprises reacting a compound of formula IIa or IIb (IIa)

(IIb)

in which formulae X and Y are as defined for formula I, with an alkanol of formula III HO—A—Het            (III)

wherein A and Het are as defined for formula I, in an inert organic solvent or diluent and in the presence of a base.

Suitable solvents for these reactions are substantially anhydrous hydrocarbons, ethers or ketones, e.g. benzene, toluene, xylene, hexane, cyclohexane, diisopropyl ether, tetrahydrofuran and dioxane. Examples of suitable bases are sodium hydride, 1,8-diazabicyclo[5.4.- 0]undec-7-ene and triethylamine.

These reactions are carried out in the temperature range from 0° to 200° C., generally at the boiling point of the reaction mixture.

The starting materials of formula IIa are known or they can be prepared by known methods, e.g. in accordance with published European patent application No. 41 623 by condensing, under basic conditions, an N-(α-isopropyl-α-methylacetamido)-2,3-pyridinecarboximide according to the following scheme:

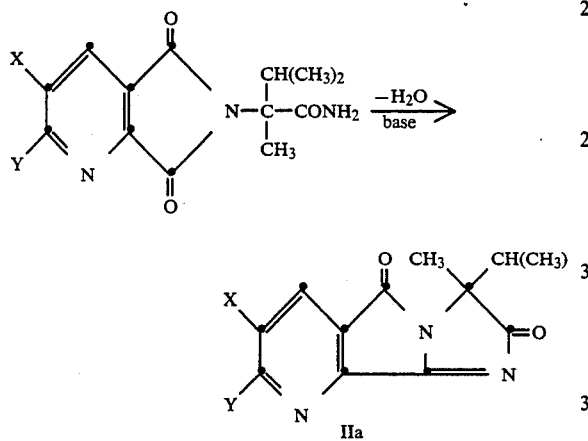

A pyridine-2,3-dicarboxylic acid α-isopropyl-α-methylacetonitrile of formula IV can be prepared in simple manner by condensing an unsaturated hydrazone with a 2-chloro- or 2-bromo-N-(α-isopropyl-α-methylacetonitrile)maleimide in accordance with the following scheme:

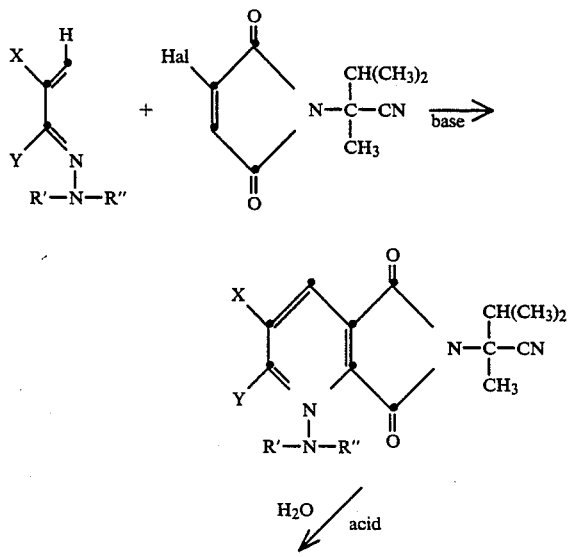

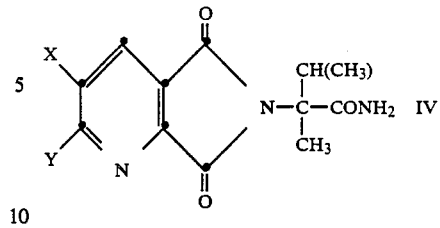

in which formulae each of R' and R" is hydrogen or $C_1$–$C_4$alkyl, Hal is chlorine or bromine, and X and Y are as defined for formula I.

The starting materials of formula IIb are obtained by converting the above N-(α-isopropyl-α-methylacetamido)-2,3-pyridinecarboximide, in the presence of a base such as sodium hydroxide solution, into the 2-(4-isopropyl-4-methyl-5-oxoimidazolidine)nicotinic acid derivative

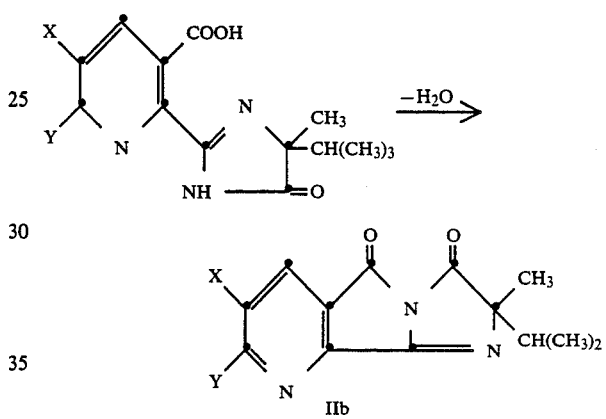

which is converted into the starting material of formula IIb (2-isopropyl-2-methyl-3H-imidazo[1',2':1,2]pyrrolo[3,4-b]pyridine-3,5-dione) by treatment with a condensing agent in an inert organic solvent, with the loss of a water molecule. Such nicotinic acid esters and the preparation thereof are described in published European patent application No. 41 623.

Examples of suitable condensing agents for this cyclisation are e.g. a molar amount of a strong acid, e.g. concentrated sulfuric acid, or of an anhydride, or a water absorbing reagent such as cyclohexanecarbodiimide, thionyl chloride or phosgene in the presence of a small amount of dimethylformamide. Condensation can also be effected by boiling the reaction mixture in a water separator.

If the reactions can not be carried out at room temperature, then they are carried out in the temperature range from 0° C. to 200° C., i.e. the reaction mixture is heated—if necessary—to its boiling point and cooled—if necessary—with ice/water or ice/brine.

Suitable bases for these reactions are particular inorganic bases such as sodium hydroxide, sodium carbonate, sodium hydride, calcium hydroxide, calcium carbonate, potassium hydroxide, potassium carbonate, ammonia and tertiary organic bases such as triethylamine.

Suitable solvents are e.g. polar, aprotic solvents which can be used by themselves or in mixtures consisting of at least two solvents.

Among the novel esters of formula I, very active nicotinic acid esters are those wherein A is a methylene or ethylene bridge which may be substituted by methyl, X is hydrogen or $C_1$–$C_3$alkyl, Y is hydrogen and Het is as defined above, and also those wherein A is the methylene, ethyl-1-ene or ethyl-2-ene bridge, X is hydrogen or $C_1$–$C_3$alkyl, Y is hydrogen and Het is an unsaturated 5- or 6-membered heterocycle which contains one to three nitrogen atoms and which may further contain one or two carbonyl groups, which heterocycle may also be fused to benzene rings and substituted by methyl.

In particular the following compounds are very effective:

4-pyridylmethyl 2-(5-isopropyl-5-methyl-4-oxo-4,5-dihydroimidazolin-2-yl)-5-methylnicotinate;

indolylethyl 5-ethyl-2-(5-isopropyl-5-methyl-4-oxo-4,5-dihydroimidazolin-2-yl)nicotinate;

indolylethyl 2-(5-isopropyl-5-methyl-4-oxo-4,5-dihydroimidazolin-2-yl)-5-methylnicotinate;

pyridin-2-ylethyl 5-ethyl-2-(5-isopropyl-5-methyl-4-oxo-4,5-dihydroimidazolin-2-yl)nicotinate;

isoindol-2-ylethyl 5-ethyl-2-(5-isopropyl-5-methyl-4-oxo-4,5-dihydroimidazolin-2-yl)nicotinate;

pyridin-2-ylmethyl 5-ethyl-2-(5-isopropyl-5-methyl-4-oxo-4,5-dihydroimidazolin-2-yl)nicotinate;

pyridin-3-ylmethyl 5-ethyl-2-(5-isopropyl-5-methyl-4-oxo-4,5-dihydroimidazolin-2-yl)nicotinate;

pyridin-4-ylmethyl 5-ethyl-2-(5-isopropyl-5-methyl-4-oxo-4,5-dihydroimidazolin-2-yl)nicotinate;

pyridin-2-ylmethyl 2-(5-isopropyl-5-methyl-4-oxo-4,5-dihydroimidazolin-2-yl)-5-methylnicotinate;

pyridin-3-ylmethyl 2-(5-isopropyl-5-methyl-4-oxo-4,5-dihydroimidazolin-2-yl)-5-methylnicotinate;

pyridin-2-ylethyl 2-(5-isopropyl-5-methyl-4-oxo-4,5-dihydroimidazolin-2-yl)nicotinate and pyridin-2-ylethyl 2-(5-isopropyl-5-methyl-4-oxo-4,5-dihydroimidazolin-2-yl)-5-methylnicotinate.

The invention relates to all diastereomeric and enantiomeric isomers of the compounds of formula I.

The compounds of formula I are usually successfully applied at concentrations of 0.05 to 4 kg/ha, in particular 0.1 to 1 kg/ha.

When used at low rates of application, the compounds of formula I have good selective growth inhibiting and selective herbicidal properties which make them most suitable for use in crops of useful plants, preferably in cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of formula I are effective even when used at very low rates of application.

The compounds of formula I have in addition pronounced plant growth inhibiting properties. The growth of both monocots and dicots is inhibited.

Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth inhibitors resides in the fact that nutrients are able increasingly to promote flower formation and fruiting, whereas vegetative growth is inhibited.

At higher rates of application of compounds of formula I, all tested plants are so severely damaged in their development that they die.

The invention also relates to herbicidal and plant growth regulating compositions which contain a novel compound of formula I, and also to methods of controlling weeds pre- and postemergence and of inhibiting the growth of monocots and dicots, especially grasses, tropical cover crops and tobacco plant suckers.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powder, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compound (surfactants).

Suitable solvents ae: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstitued or substituted ammonium salts and contain a $C_8$–$C_{22}$alkyl radical which also includes the alkyl moiety of acyl radicals, e.g. the sodium or calcium salt of lignosulfonic acid, dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp. Ridgewood, N.J., 1981;

H. Stache, "Tensid-Taschenbuch" (Handbood of Surfactants), C. Hanser Verlag, Munich & Vienna, 1981.

The ready-for-use preparations usually contain 0.1 to 95%, preferably 0.1 to 80%, of a compound of formula I, 1 to 99.9% of a solid or liquid adjuvant, and 0 to 25%, preferably 0.1 to 25%, of a surfactant.

Preferred formulations are composed in particular of the following constituents (%=percentage by weight):

Emulsifiable concentrates compound of formula I: 1 to 20%, preferably 5 to 10%
surfactant: 5 to 30%, preferably 10 to 20%
liquid carrier: 50 to 94%, preferably 70 to 85%

Dusts compound of formula I: 0.1 to 10%, preferably 0.1 to 1%
solid carrier: 99.9 to 90%, preferably 99.9 to 99%

Suspension concentrates compound of formula I: 5 to 75%, preferably 10 to 50%
water: 94 to 25%, preferably 90 to 30%
surfactant: 1 to 40%, preferably 2 to 30%

Wettable powders compound of formula I: 0.5 to 90%, preferably 1 to 80%
surfactant: 0.5 to 20%, preferably 1 to 15%
solid carrier: 5 to 95%, preferably 15 to 90%

Granulates compound of formula I: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001% of active ingredient. The rates of application are usually from 0.005 to 5 kg a.i./ha.

The compositions may also contain further ingredients such as stabilisers, antifoams, viscosity regulators, binders, tackifiers, as well as fertilisers and other compounds for obtaining special effects.

The following Example illustrates the preparation of a compound of formula I. Further compounds prepared in corresponding manner are listed in the subsequent Table.

EXAMPLE 1

Preparation of 4-pyridylmethyl 2-(5-isopropyl-5-methyl-4-oxo-4,5-dihydroimidazolin-2-yl)-5-methylnicotinate

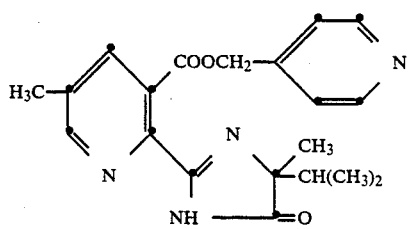

7.71 g (=0.03 mole) of 3,5-dioxo-2-isopropyl-2,8-dimethyl-2,3-dihydroimidazo[1',2':1,2]-5H-pyrrolo[3,4-b]pyridine, 3.27 g of 4-hydroxymethylpyridine and 4 drops of 1,8-diazabicyclo[5.4.0]undec-7-ene (DBU) are heated under reflux overnight in 150 ml of toluene. The solvent is then evaporated off and the residue is crystallised from a mixture of methylene chloride and hexane. Yield: 9.5 g (=87% of theory). Melting point: 182°–184° C.

The 3,5-dioxo-2-isopropyl-2,8-dimethyl-2,3-dihydroimidazo[1',2':1,2]-5-H-pyrrolo[3,4-b]pyridine required as starting material is prepared as follows:

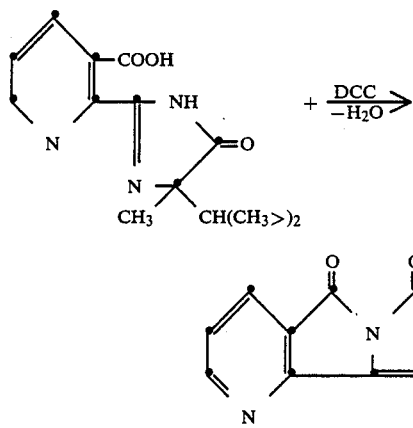

With stirring, 13.1 g (0.05 mole) of 2-(5-isopropyl-5-methyl-4-oxo-4,5-dihydroimidazolin-2-yl)nicotinic acid are added to a solution of 11.1 g of dicyclohexylcarbodiimide (DCC) in 100 ml of methylene chloride. Stirring is continued for a further 2 hours at room temperature. The resultant dicyclohexylurea is removed by suction filtration and the residue is washed with a small amount of methylene chloride. The filtrate is concentrated by evaporation and the residue is recrystallised from a mixture of ethyl acetate and hexane, affording the title product in 86% yield (10.4 g) in the form of crystals which melt at 132°–133° C.

The following starting materials are obtained in analogous manner:

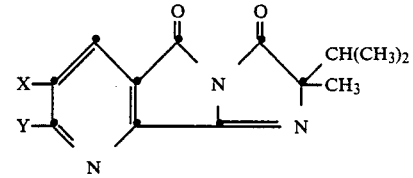

| X | X | Physical data |
|---|---|---|
| nC₃H₇ | H | m.p. 132–133° C. |
| CH(CH₃)₂ | H | m.p. 145–146° C. |
| C₂H₅ | H | m.p. 136–138° C. |
| n-C₄H₉ | H | m.p. 116–119° C. |
| CH₃ | H | m.p. 129–131° C. |

The following compounds are obtained in the same manner by using the corresponding starting materials:

TABLE 1

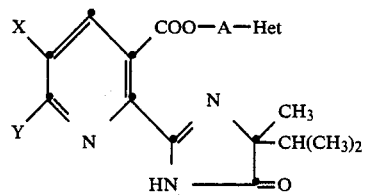

| Comp. | X | Y | A | Het | m.p. |
|---|---|---|---|---|---|
| 1.001 | CH₃ | H | CH₂ | pyridin-4-yl | 182–184° C. Example 1 |
| 1.002 | CH₃ | H | CH₂CH₂ | indol-2-yl | 146–149° C. |
| 1.003 | C₂H₅ | H | CH₂CH₂ | indol-2-yl | 166–168° C. |
| 1.004 | C₂H₅ | H | CH₂CH₂ | pyridin-2-yl | resin |
| 1.005 | C₂H₅ | H | CH₂CH₂ | isoindol-1,3-dion-2-yl | 130–131° C. |
| 1.006 | C₂H₅ | H | CH₂ | pyridin-2-yl | 80–82° C. |
| 1.007 | C₂H₅ | H | CH₂ | pyridin-3-yl | 123–124° C. |
| 1.008 | C₂H₅ | H | CH₂ | pyridin-4-yl | 135–137° C. |
| 1.009 | CH₃ | H | CH₂ | pyridin-3-yl | 133–134° C. |
| 1.010 | CH₃ | H | CH₂ | pyridin-2-yl | 172–173° C. |
| 1.011 | H | H | CH₂CH₂ | pyridin-2-yl | 105–106° C. |
| 1.012 | CH₃ | H | CH₂CH₂ | pyridin-2-yl | 119–122° C. |
| 1.013 | H | H | CH(CH₃) | pyridin-4-yl | |
| 1.014 | (CH=CH)₂ | | CH₂CH₂ | pyridin-4-yl | |
| 1.015 | (CH=CH)₂ | | CH₂ | pyridin-4-yl | |
| 1.016 | (CH=CH)₂ | | CH₂ | pyridazin-2-yl | |
| 1.017 | (CH=CH)₂ | | CH₂ | pyrrol-1-yl | |
| 1.018 | H | H | CH₂CH₂ | pyrrol-1-yl | |
| 1.019 | H | H | CH₂ | pyrrol-1-yl | |
| 1.020 | H | H | CH₂CH₂ | imidazol-1-yl | |
| 1.021 | CH₃ | H | CH₂ | imidazol-1-yl | |
| 1.022 | H | H | CH₂ | 1H—1,2,4-triazol-1-yl | |
| 1.023 | CH₃ | H | CH₂CH₂ | 1H—1,2,4-triazol-1-yl | |
| 1.024 | CH₃ | H | CH₂ | 1H—1,3,4-triazol-1-yl | |
| 1.025 | H | H | CH₂CH₂ | 1H—1,3,4-triazol-1-yl | |
| 1.026 | H | H | CH₂ | pyrimidin-4-yl | |
| 1.027 | CH₃ | H | CH(CH₃)CH₂ | pyrimidin-4-yl | |
| 1.028 | CH₃ | H | CH₂ | pyrimidin-2-yl | |
| 1.029 | C₂H₅ | H | CH₂ | pyrimidin-2-yl | |
| 1.030 | H | H | CH₂CH₂ | indol-3-yl | |

TABLE 1-continued

| Comp. | X | Y | A | Het | m.p. |
|---|---|---|---|---|---|
| 1.031 | $CH_3$ | H | $CH_2$ | indol-3-yl | |
| 1.032 | $(CH=CH)_2$ | | $CH_2$ | 4-methylpyridin-2-yl | |
| 1.033 | $(CH=CH)_2$ | | $CH_2$ | pyrimidin-2-yl | |
| 1.034 | $(CH=CH)_2$ | | $CH_2$ | indol-2-yl | |
| 1.035 | $CH_3$ | H | $CH_2$ | tetrahydrofur-2-yl | 113–115° C. |
| 1.036 | $CH_3$ | H | $CH_2CH_2$ | indol-2-yl | 146–149° C. |
| 1.037 | H | H | $-C_3H_6-$ | pyrazol-4-yl | 168–172° C. |
| 1.038 | $CH_3$ | H | $CH_2CH_2$ | pthalimido | 151–153° C. |
| 1.039 | $C_2H_5$ | H | $CH_2$ | furfurol-5-yl | resin |
| 1.040 | H | H | $C_3H_6$ | 1,2-oxazol-4-yl | oil |
| 1.041 | H | H | $CH_2$ | pyridin-2-yl | 111–112° C. |
| 1.042 | H | H | $CH_2$ | pyridin-3-yl | 137–138° C. |
| 1.043 | H | H | $CH_2$ | pyridin-4-yl | 155–157° C. |
| 1.044 | H | H | $CH_2CH_2$ | indol-2-yl | resin |
| 1.045 | H | H | $CH_2CH_2$ | pthalimido | resin |
| 1.046 | H | H | $CH_2$ | tetrahydrofur-2-yl | |
| 1.047 | H | H | $C_3H_6$ | 1-phenylpyrazol-4-yl | 118–119° C. |
| 1.048 | H | H | $C_3H_6$ | 1-methylpyrazol-4-yl | 134–135° C. |
| 1.049 | H | H | $C_3H_6$ | 1-ethylpyrazol-4-yl | 87–88° C. |
| 1.050 | $C_2H_5$ | H | $C_3H_6$ | 1-methylpyrazol-4-yl | 90–92° C. |
| 1.051 | $C_2H_5$ | H | $C_3H_6$ | 1,2-oxazol-4-yl | 90–92° C. |
| 1.052 | $C_2H_5$ | H | $C_3H_6$ | 1-ethylpyrazol-4-yl | resin |
| 1.053 | $(CH=CH)_2$ | | $CH_2$ | 1-ethylpyrazol-4-yl | resin |
| 1.054 | $C_3H_7n$ | H | $CH_2$ | pyridin-4-yl | 110° C. |
| 1.055 | $C_3H_7n$ | H | $C_2H_4$ | pyridin-4-yl | 108° C. |
| 1.056 | $C_3H_7n$ | H | $CH_2$ | tetrahydrofur-2-yl | 87–90° C. |
| 1.057 | H | H | $CH_2CH_2$ | 1,2-oxazol-4-yl | resin |
| 1.058 | $CH_3$ | H | $CH_2CH_2$ | 1,2-oxazol-4-yl | oil |
| 1.059 | $C_2H_5$ | H | $CH_2CH_2$ | 1,2-oxazol-4-yl | oil |
| 1.060 | $(CH=CH)_2$ | | $CH_2CH_2$ | 1,2-oxazol-4-yl | |
| 1.061 | Cl | H | $CH_2CH_2$ | 1,2-oxazol-4-yl | |
| 1.062 | CH=CCl—CH=CH | | $CH_2CH_2$ | 1,2-oxazol-4-yl | |
| 1.063 | Br | H | $CH_2CH_2$ | 1,2-oxazol-4-yl | |
| 1.064 | | $CH(CH_3)_2$ | $CH_2CH_2$ | 1,2-oxazol-4-yl | |
| 1.065 | H | H | $CH_2CH_2$ | pyrazol-4-yl | |
| 1.066 | H | H | $CH_2CH_2$ | 1-methylpyrazol-4-yl | |
| 1.067 | H | H | $CH_2CH_2$ | 1-ethylpyrazol-4-yl | |
| 1.068 | H | H | $CH_2CH_2$ | 1-phenylpyrazol-4-yl | 131–132° C. |
| 1.069 | $CH_3$ | H | $CH_2CH_2$ | pyrazol-4-yl | |
| 1.070 | $CH_3$ | H | $CH_2CH_2$ | 1-methylpyrazol-4-yl | |
| 1.071 | $CH_3$ | H | $CH_2CH_2$ | 1-ethylpyrazol-4-yl | |
| 1.072 | $CH_3$ | H | $CH_2CH_2$ | 1-phenylpyrazol-4-yl | |
| 1.073 | $C_2H_5$ | H | $CH_2CH_2$ | pyrazol-1-yl | 148–151° C. |
| 1.074 | $C_2H_5$ | H | $CH_2CH_2$ | 1-methylpyrazol-4-yl | |
| 1.075 | $C_2H_5$ | H | $CH_2CH_2$ | 1-ethylpyrazol-4-yl | |
| 1.076 | $C_2H_5$ | H | $CH_2CH_2$ | 1-phenylpyrazol-4-yl | vitreous |
| 1.077 | $(CH=CH)_2$ | | $CH_2CH_2$ | pyrazol-4-yl | |
| 1.078 | $(CH=CH)_2$ | | $CH_2CH_2$ | 1-methylpyrazol-4-yl | |
| 1.079 | $(CH=CH)_2$ | | $CH_2CH_2$ | 1-ethylpyrazol-4-yl | |
| 1.080 | $(CH=CH)_2$ | | $CH_2CH_2$ | 1-phenylpyrazol-4-yl | solid |
| 1.081 | Cl | H | $CH_2CH_2$ | pyrazol-4-yl | |
| 1.082 | Cl | H | $CH_2CH_2$ | 1-methylpyrazol-4-yl | |
| 1.083 | Cl | H | $CH_2CH_2$ | 1-ethylpyrazol-4-yl | |
| 1.084 | Cl | H | $CH_2CH_2$ | 1-phenylpyrazol-4-yl | |
| 1.085 | CH=CCl—CH=CH | | $CH_2CH_2$ | pyrazol-4-yl | |
| 1.086 | CH=CCl—CH=CH | | $CH_2CH_2$ | 1-methylpyrazol-4-yl | |
| 1.087 | CH=CCl—CH=CH | | $CH_2CH_2$ | 1-ethylpyrazol-4-yl | |
| 1.088 | CH=CCl—CH=CH | | $CH_2CH_2$ | 1-phenylpyrazol-4-yl | |
| 1.089 | Br | H | $CH_2CH_2$ | pyrazol-4-yl | |
| 1.090 | Br | H | $CH_2CH_2$ | 1-methylpyrazol-4-yl | |
| 1.091 | Br | H | $CH_2CH_2$ | 1-ethylpyrazol-4-yl | |
| 1.092 | Br | H | $CH_2CH_2$ | 1-phenylpyrazol-4-yl | |
| 1.093 | H | $CH(CH_3)_2$ | $CH_2CH_2$ | pyrazol-4-yl | |
| 1.094 | H | $CH(CH_3)_2$ | $CH_2CH_2$ | 1-methylpyrazol-4-yl | |
| 1.095 | H | $CH(CH_3)_2$ | $CH_2CH_2$ | 1-ethylpyrazol-4-yl | |
| 1.096 | H | $CH(CH_3)_2$ | $CH_2CH_2$ | 1-phenylpyrazol-4-yl | |
| 1.097 | H | H | $CH_2CH_2$ | 3,5-dibromooxazol-4-yl | |
| 1.098 | $CH_3$ | H | $CH_2CH_2$ | 3,5-dibromooxazol-4-yl | |
| 1.099 | $C_2H_5$ | H | $CH_2CH_2$ | 3,5-dibromooxazol-4-yl | |
| 1.100 | $(CH=CH)_2$ | | $CH_2CH_2$ | 3,5-dibromooxazol-4-yl | |
| 1.101 | Cl | H | $CH_2CH_2$ | 3,5-dibromooxazol-4-yl | |

TABLE 1-continued

| Comp. | X | Y | A | Het | m.p. |
|---|---|---|---|---|---|
| 1.102 | CH=CCl—CH=CH | | CH₂CH₂ | 3,5-dibromooxazol-4-yl | |
| 1.103 | Br | H | CH₂CH₂ | 3,5-dibromooxazol-4-yl | |
| 1.104 | H | CH(CH₃)₂ | CH₂CH₂ | 3,5-dibromooxazol-4-yl | |
| 1.105 | H | H | CH₂ | benzimidazol-2-yl | |
| 1.106 | CH₃ | H | CH₂ | benzimidazol-2-yl | |
| 1.107 | C₂H₅ | H | CH₂ | benzimidazol-2-yl | |
| 1.108 | (CH=CH)₂ | | CH₂ | benzimidazol-2-yl | |
| 1.109 | Cl | H | CH₂ | benzimidazol-2-yl | |
| 1.110 | CH=CCl—CH=CH | | CH₂ | benzimidazol-2-yl | |
| 1.111 | Br | H | CH₂ | benzimidazol-2-yl | |
| 1.112 | H | CH(CH₃)₂ | CH₂ | benzimidazol-2-yl | |
| 1.113 | H | H | CH₂ | imidazol-2-yl | |
| 1.114 | CH₃ | H | CH₂ | imidazol-2-yl | |
| 1.115 | C₂H₅ | H | CH₂ | imidazol-2-yl | |
| 1.116 | (CH=CH)₂ | | CH₂ | imidazol-2-yl | |
| 1.117 | Cl | H | CH₂ | imidazol-2-yl | |
| 1.118 | CH=CCl—CH=CH | | CH₂ | imidazol-2-yl | |
| 1.119 | Br | H | CH₂ | imidazol-2-yl | |
| 1.120 | H | CH(CH₃)₂ | CH₂ | imidazol-2-yl | |
| 1.121 | H | H | CH₂ | benzoxazol-2-yl | |
| 1.122 | CH₃ | H | CH₂ | benzoxazol-2-yl | |
| 1.123 | C₂H₅ | H | CH₂ | benzoxazol-2-yl | |
| 1.124 | (CH=CH)₂ | | CH₂ | benzoxazol-2-yl | |
| 1.125 | Cl | H | CH₂ | benzoxazol-2-yl | |
| 1.126 | CH=CCl—CH=CH | | CH₂ | benzoxazol-2-yl | |
| 1.127 | Br | H | CH₂ | benzoxazol-2-yl | |
| 1.128 | H | CH(CH₃)₂ | CH₂ | benzoxazol-2-yl | |
| 1.129 | H | H | CH(CH₃)CH₂ | 3-hydroxy-1,2-oxazol-5-yl | |
| 1.130 | CH₃ | H | CH(CH₃)CH₂ | 3-hydroxy-1,2-oxazol-5-yl | |
| 1.131 | C₂H₅ | H | CH(CH₃)CH₂ | 3-hydroxy-1,2-oxazol-5-yl | |
| 1.132 | (CH=CH)₂ | | CH(CH₃)CH₂ | 3-hydroxy-1,2-oxazol-5-yl | |
| 1.133 | Cl | H | CH(CH₃)CH₂ | 3-hydroxy-1,2-oxazol-5-yl | |
| 1.134 | CH=CCl—CH=CH | | CH(CH₃)CH₂ | 3-hydroxy-1,2-oxazol-5-yl | |
| 1.135 | Br | H | CH(CH₃)CH₂ | 3-hydroxy-1,2-oxazol-5-yl | |
| 1.136 | H | CH(CH₃)₂ | CH(CH₃)CH₂ | 3-hydroxy-1,2-oxazol-5-yl | |
| 1.137 | H | H | (CH₂)₄ | 2-methylpyridin-4-yl | |
| 1.138 | CH₃ | H | (CH₂)₄ | 2-methylpyridin-4-yl | |
| 1.139 | C₂H₅ | H | (CH₂)₄ | 2-methylpyridin-4-yl | |
| 1.140 | (CH=CH)₂ | | (CH₂)₄ | 2-methylpyridin-4-yl | |
| 1.141 | Cl | H | (CH₂)₄ | 2-methylpyridin-4-yl | |
| 1.142 | CH=CCl—CH=CH | | (CH₂)₄ | 2-methylpyridin-4-yl | |
| 1.143 | Br | H | (CH₂)₄ | 2-methylpyridin-4-yl | |
| 1.144 | H | CH(CH₃)₂ | (CH₂)₄ | 2-methylpyridin-4-yl | |
| 1.145 | H | H | CH₂ | 3-methyl-1,2,4-triazol-5-yl | |
| 1.146 | CH₃ | H | CH₂ | 3-methyl-1,2,4-triazol-5-yl | |
| 1.147 | C₂H₅ | H | CH₂ | 3-methyl-1,2,4-triazol-5-yl | |
| 1.148 | (CH=CH)₂ | | CH₃ | 3-methyl-1,2,4-triazol-5-yl | |
| 1.149 | Cl | H | CH₂ | 3-methyl-1,2,4-triazol-5-yl | |
| 1.150 | CH=CCl—CH=CH | | CH₂ | 3-methyl-1,2,4-triazol-5-yl | |
| 1.151 | Br | H | CH₂ | 3-methyl-1,2,4-triazol-5-yl | |
| 1.152 | H | CH(CH₃)₂ | CH₂ | 3-methyl-1,2,4-triazol-5-yl | |
| 1.153 | H | H | CH₂ | 1,3,4-oxadiazol-2-yl | |
| 1.154 | CH₃ | H | CH₂ | 1,3,4-oxadiazol-2-yl | |
| 1.155 | C₂H₅ | H | CH₂ | 1,3,4-oxadiazol-2-yl | |
| 1.156 | (CH=CH)₂ | | CH₂ | 1,3,4-oxadiazol-2-yl | |
| 1.157 | Cl | H | CH₂ | 1,3,4-oxadiazol-2-yl | |
| 1.158 | CH=CCl—CH=CH | | CH₂ | 1,3,4-oxadiazol-2-yl | |
| 1.159 | Br | H | CH₂ | 1,3,4-oxadiazol-2-yl | |
| 1.160 | H | CH(CH₃)₂ | CH₂ | 1,3,4-oxadiazol-2-yl | |
| 1.161 | H | H | CH₂ | 4-nitropyridin-2-yl | |
| 1.162 | CH₃ | H | CH₂ | 4-nitropyridin-2-yl | |
| 1.163 | C₂H₅ | H | CH₂ | 4-nitropyridin-2-yl | |
| 1.164 | (CH=CH)₂ | H | CH₂ | 4-nitropyridin-2-yl | |
| 1.165 | Cl | H | CH₂ | 4-nitropyridin-2-yl | |
| 1.166 | CH=CCl—CH=CH | | CH₂ | 4-nitropyridin-2-yl | |
| 1.167 | Br | H | CH₂ | 4-nitropyridin-2-yl | |
| 1.168 | H | CH(CH₃)₂ | CH₂ | 4-nitropyridin-2-yl | |
| 1.169 | H | H | CH₂ | 4-chloropyridin-2-yl | |
| 1.170 | CH₃ | H | CH₂ | 4-chloropyridin-2-yl | |
| 1.171 | C₂H₅ | H | CH₂ | 4-chloropyridin-2-yl | |
| 1.172 | (CH=CH)₂ | H | CH₂ | 4-chloropyridin-2-yl | |

TABLE 1-continued

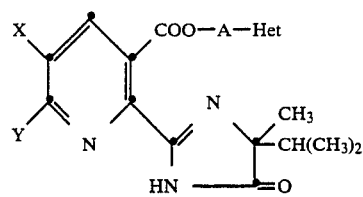

| Comp. | X | Y | A | Het | m.p. |
|---|---|---|---|---|---|
| 1.173 | Cl | H | CH$_2$ | 4-chloropyridin-2-yl | |
| 1.174 | CH=CCl—CH=CH | | CH$_2$ | 4-chloropyridin-2-yl | |
| 1.175 | Br | H | CH$_2$ | 4-chloropyridin-2-yl | |
| 1.176 | H | CH(CH$_3$)$_2$ | CH$_2$ | 4-chloropyridin-2-yl | |
| 1.177 | H | H | CH$_2$ | 2-chloropyridin-6-yl | |
| 1.178 | CH$_3$ | H | CH$_2$ | 2-chloropyridin-6-yl | |
| 1.179 | C$_2$H$_5$ | H | CH$_2$ | 2-chloropyridin-6-yl | |
| 1.180 | (CH=CH)$_2$ | | CH$_2$ | 2-chloropyridin-6-yl | |
| 1.181 | Cl | H | CH$_2$ | 2-chloropyridin-6-yl | |
| 1.182 | CH=CCl—CH=CH | | CH$_2$ | 2-chloropyridin-6-yl | |
| 1.183 | Br | H | CH$_2$ | 2-chloropyridin-6-yl | |
| 1.184 | H | CH(CH$_3$)$_2$ | CH$_2$ | 2-chloropyridin-6-yl | |
| 1.185 | H | H | CH$_2$ | quinolin-2-yl | |
| 1.186 | CH$_3$ | H | CH$_2$ | quinolin-2-yl | |
| 1.187 | C$_2$H$_5$ | H | CH$_2$ | quinolin-2-yl | |
| 1.188 | (CH=CH)$_2$ | | CH$_2$ | quinolin-2-yl | |
| 1.189 | Cl | H | CH$_2$ | quinolin-2-yl | |
| 1.190 | CH=CCl—CH=CH | | CH$_2$ | quinolin-2-yl | |
| 1.191 | Br | H | CH$_2$ | quinolin-2-yl | |
| 1.192 | H | CH(CH$_3$)$_2$ | CH$_2$ | quinolin-2-yl | |
| 1.193 | H | H | CH$_2$ | 4-nitroquinolin-2-yl | |
| 1.194 | CH$_3$ | H | CH$_2$ | 4-nitroquinolin-2-yl | |
| 1.195 | C$_2$H$_4$ | H | CH$_2$ | 4-nitroquinolin-2-yl | |
| 1.196 | (CH=CH)$_2$ | | CH$_2$ | 4-nitroquinolin-2-yl | |
| 1.197 | Cl | H | CH$_2$ | 4-nitroquinolin-2-yl | |
| 1.198 | CH=CCl—CH=CH | | CH$_2$ | 4-nitroquinolin-2-yl | |
| 1.199 | Br | H | CH$_2$ | 4-nitroquinolin-2-yl | |
| 1.200 | H | CH(CH$_3$)$_2$ | CH$_2$ | 4-nitroquinolin-2-yl | |
| 1.201 | H | H | CH$_2$ | quinoxalin-2-yl | |
| 1.202 | CH$_3$ | H | CH$_2$ | quinoxalin-2-yl | |
| 1.203 | C$_2$H$_5$ | H | CH$_2$ | quinoxalin-2-yl | |
| 1.204 | (CH=CH)$_2$ | | CH$_2$ | quinoxal-2-yl | |
| 1.205 | Cl | H | CH$_2$ | quinoxal-2-yl | |
| 1.206 | CH=CCl—CH=CH | | CH$_2$ | quinoxal-2-yl | |
| 1.207 | Br | H | CH$_2$ | quinoxal-2-yl | |
| 1.208 | H | CH(CH$_3$)$_2$ | CH$_2$ | quinoxal-2-yl | |
| 1.209 | H | H | CH(CH$_3$)CH$_2$ | 4-chloropyridin-2-yl | |
| 1.210 | CH$_3$ | H | CH(CH$_3$)CH$_2$ | 4-chloropyridin-2-yl | |
| 1.211 | C$_2$H$_5$ | H | CH(CH$_3$)CH$_2$ | 4-chloropyridin-2-yl | |
| 1.212 | (CH=CH) | H | CH(CH$_3$)CH$_2$ | 4-chloropyridin-2-yl | |
| 1.213 | Cl | H | CH(CH$_3$)CH$_2$ | 4-chloropyridin-2-yl | |
| 1.214 | CH=CCl—CH=CH | | CH(CH$_3$)CH$_2$ | 4-chloropyridin-2-yl | |
| 1.215 | Br | H | CH(CH$_3$)CH$_2$ | 4-chloropyridin-2-yl | |
| 1.216 | H | CH(CH$_3$)$_2$ | CH(CH$_3$)CH$_2$ | 4-chloropyridin-2-yl | |
| 1.217 | H | H | CH$_2$ | 2,4-dichloropyridin-6-yl | |
| 1.218 | CH$_3$ | H | CH$_2$ | 2,4-dichloropyridin-6-yl | |
| 1.219 | C$_2$H$_5$ | H | CH$_2$ | 2,4-dichloropyridin-6-yl | |
| 1.220 | (CH=CH)$_2$ | | CH$_2$ | 2,4-dichloropyridin-6-yl | |
| 1.221 | Cl | H | CH$_2$ | 2,4-dichloropyridin-6-yl | |
| 1.222 | CH=CCl—CH=CH | | CH$_2$ | 2,4-dichloropyridin-6-yl | |
| 1.223 | Br | H | CH$_2$ | 2,4-dichloropyridin-6-yl | |
| 1.224 | H | CH(CH$_3$)$_2$ | CH$_2$ | 2,4-dichloropyridin-6-yl | |
| 1.225 | H | H | CH$_2$ | 4-methoxypyrimidin-2-yl | |
| 1.226 | CH$_3$ | H | CH$_2$ | 4-methoxypyrimidin-2-yl | |
| 1.227 | C$_2$H$_5$ | H | CH$_2$ | 4-methoxypyrimidin-2-yl | |
| 1.228 | (CH=CH)$_2$ | | CH$_2$ | 4-methoxypyrimidin-2-yl | |
| 1.229 | Cl | H | CH$_2$ | 4-methoxypyrimidin-2-yl | |
| 1.230 | CH=CCl—CH=CH | | CH$_2$ | 4-methoxypyrimidin-2-yl | |
| 1.231 | Br | H | CH$_2$ | 4-methoxypyrimidin-2-yl | |
| 1.232 | H | CH(CH$_3$)$_2$ | CH$_2$ | 4-methoxypyrimidin-2-yl | |
| 1.233 | H | H | CH(CH$_3$)CH$_2$ | pyridin-4-yl | |
| 1.234 | CH$_3$ | H | CH(CH$_3$)CH$_2$ | pyridin-4-yl | |
| 1.235 | C$_2$H$_5$ | H | CH(CH$_3$)CH$_2$ | pyridin-4-yl | |
| 1.236 | (CH=CH)$_2$ | | CH(CH$_3$)CH$_2$ | pyridin-4-yl | |
| 1.237 | Cl | H | CH(CH$_3$)CH$_2$ | pyridin-4-yl | |
| 1.238 | CH=CCl—CH—CH | | CH(CH$_3$)CH$_2$ | pyridin-4-yl | |
| 1.239 | Br | H | CH(CH$_3$)CH$_2$ | pyridin-4-yl | |
| 1.240 | H | CH(CH$_3$)$_2$ | CH(CH$_3$)CH$_2$ | pyridin-4-yl | |
| 1.241 | H | H | CH$_2$ | 4-methoxypyrimidin-2-yl | |
| 1.242 | CH$_3$ | H | CH$_2$ | 4-methoxypyrimidin-2-yl | |
| 1.243 | C$_2$H$_5$ | H | CH$_2$ | 4-methoxypyrimidin-2-yl | |

TABLE 1-continued

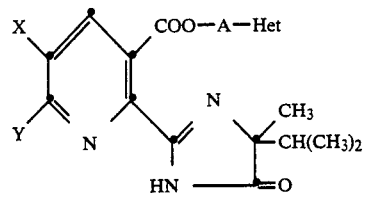

| Comp. | X | Y | A | Het | m.p. |
|---|---|---|---|---|---|
| 1.244 | (CH=CH)₂ | | CH₂ | 4-methoxypyrimidin-2-yl | |
| 1.245 | Cl | H | CH₂ | 4-methoxypyrimidin-2-yl | |
| 1.246 | CH=CCl—CH=CH | | CH₂ | 4-methoxypyrimidin-2-yl | |
| 1.247 | Br | H | CH₂ | 4-methoxypyrimidin-2-yl | |
| 1.248 | H | CH(CH₃)₂ | CH₂ | 4-methoxypyrimidin-2-yl | |
| 1.249 | H | H | CH₂ | pyrimidin-2-yl | |
| 1.250 | CH₃ | H | CH₂ | pyrimidin-2-yl | |
| 1.251 | C₂H₅ | H | CH₂ | pyrimidin-2-yl | |
| 1.252 | (CH=CH)₂ | | CH₂ | pyrimidin-2-yl | |
| 1.253 | Cl | H | CH₂ | pyrimidin-2-yl | |
| 1.254 | CH=CCl—CH=CH | | CH₂ | pyrimidin-2-yl | |
| 1.255 | Br | H | CH₂ | pyrimidin-2-yl | |
| 1.256 | H | CH(CH₃)₂ | CH₂ | pyrimidin-2-yl | |
| 1.257 | H | H | CH(CH₃) | pyridin-4-yl | |
| 1.258 | CH₃ | H | CH₂ | pyridin-4-yl | |
| 1.259 | C₂H₅ | H | CH₂ | pyridin-4-yl | |
| 1.260 | (CH=CH)₂ | | CH₂ | pyridin-4-yl | |
| 1.261 | Cl | H | CH₂ | pyridin-4-yl | |
| 1.262 | CH=CCl—CH=CH | | CH₂ | pyridin-4-yl | |
| 1.263 | Br | H | CH₂ | pyridin-4-yl | |
| 1.264 | H | CH(CH₃)₂ | CH₂ | pyridin-4-yl | |
| 1.265 | H | H | CH₂ | 1,3,4-triazin-5-on-2-yl | |
| 1.266 | CH₃ | H | CH₂ | 1,3,4-triazin-5-on-2-yl | |
| 1.267 | C₂H₅ | H | CH₂ | 1,3,4-triazin-5-on-2-yl | |
| 1.268 | (CH=CH)₂ | | CH₂ | 1,3,4-triazin-5-on-2-yl | |
| 1.269 | Cl | H | CH₂ | 1,3,4-triazin-5-on-2-yl | |
| 1.270 | CH=CCl—CH=CH | | CH₂ | 1,3,4-triazin-5-on-2-yl | |
| 1.271 | Br | H | CH₂ | 1,3,4-triazin-5-on-2-yl | |
| 1.272 | H | CH(CH₃)₂ | CH₂ | 1,3,4-triazin-5-on-2-yl | |
| 1.273 | C₂H₅ | H | —(CH₂)₃ | 1-phenylpyrazol-4-yl | 143–147° C. |
| 1.274 | (CH=CH)₂ | | (CH₂)₃ | 1H—pyrazol-4-yl | solid |
| 1.275 | (CH=CH)₂ | | (CH₂)₃ | 1-methylpyrazol-4-yl | 117–118° C. |
| 1.276 | (CH=CH)₂ | | (CH₂)₃ | 1-phenylpyrazol-4-yl | 128–131° C. |
| 1.277 | CH₃ | H | CH₂ | tetrahydropyran-2-yl | 106–109° C. |
| 1.278 | CH₃ | H | CH₂CH₂ | pyrazol-1-yl | 102–104° C. |
| 1.279 | C₂H₅ | H | CH₂CH₂ | pyrimidin-5-yl | 120–122° C. |
| 1.280 | C₂H₅ | H | CH₂ | 5-(4,5-dihydro-3-methyl-thio-6-tert-butyl-1,3-triazin-5-on-2-yl-hydrazine oxime)furfur-2-yl | oil |

FORMULATION EXAMPLES

EXAMPLE 2

Formulation Examples for compounds of formula I (percentages are by weight)

(a) Wettable powders

| | (a) | (b) | (c) |
|---|---|---|---|
| compound of Table 1 | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

(b) Emulsifiable concentrates

| | (a) | (b) |
|---|---|---|
| compound of Table 1 | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

(c) Dusts

| | (a) | (b) |
|---|---|---|
| compound of Table 1 | 0.1% | 1% |
| talcum | 99.9% | — |
| kaolin | — | 99% |

Dusts which are ready for use are obtained by mixing the active ingredient with the carrier, and grinding the mixture in a suitable mill.

(d) Extruder granulates

|  | (a) | (b) |
| --- | --- | --- |
| compound of Table 1 | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

(e) Coated granulate

| compound of Table 1 | 3% |
| --- | --- |
| polyethylene glycol (mol. wt. 200) | 2% |
| kaolin | 94% |

The finely ground active ingredient is uniformly applied, in a mixer, to the kaolin moistened with polyethylene glycol. Non-dusty coated granulates are obtained in this manner.

(f) Suspension concentrates

|  | (a) | (b) |
| --- | --- | --- |
| compound of Table 1 | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

(g) Salt solution

| compound of Table 1 | 5% |
| --- | --- |
| isopropylamine | 1% |
| octylphenol polyethylene glycol ether (78 moles of ethylene oxide) | 3% |
| water | 91% |

BIOLOGICAL EXAMPLES

EXAMPLE 3

Preemergence Herbicidal Action

In a greenhouse, immediately after sowing the test plants in seed dishes, the surface of the soil is treated with an aqueous dispersion of the test compounds, obtained from a 25% emulsifiable concentrate. Concentrations of 4 kg of test compound per hectare are applied. The seed dishes are kept in the greenhouse at 22°–25° C. and 50–70% relative humidity. The test is evaluated 3 weeks later in accordance with the following rating:

| 1 | plant has not germinated or it has died |
| --- | --- |

-continued

| 2–3 | very severe damage |
| --- | --- |
| 4 | severe damage |
| 5 | moderate damage, stunted growth |
| 6 | damage, the plant can regenerate |
| 7–8 | slight damage |
| 9 | normal growth, as untreated plants |

In this test, the compounds of Table 1 exhibit strong herbicidal activity.

EXAMPLE 4

Postemergence Herbicidal Action (Contact Herbicide)

A number of weeds, both mono- and dicotyledonous, are sprayed postemergence in the 4- to 6-leaf stage with an aqueous active ingredient dispersion at a rate of 4 kg of test compound per hectare and kept at 24°–26° C. and 45–60% relative humidity. The test is evaluated 15 days later in accordance with the same rating as employed above. In this test, the compounds of Table 1 also exhibit strong to very strong herbicidal activity.

EXAMPLE 5

Preemergence Herbicidal Action

Plastic pots are filled with expanded vermiculite (density: 0.135 g/cm$^3$; water-absorbing capacity: 0.565 l/l). After the non-adsorptive vermiculite has been saturated with an aqueous emulsion in deionised water which contains the test compound in a concentration of 70.8 ppm, seeds of the following plants are sown on the surface: Nasturtium officinalis, Agrostis tenuis, Stellaria media and Digitaria sanguinalis. The pots are then kept in a climatic chamber at 20° C., an illumination of about 20 klux and a relative humidity of 70%. During the germinating phase of 4 to 6 days, the pots are covered with lightpermeable material and watered with deionised water to increase the local humidity. After the 5th day, 0,5% of a commercial liquid fertiliser (Greenzit ®) is added to the water. The test is evaluated 12 days after sowing and the action on the plants is assessed in accordance with the rating indicated in Example 3.

The results are given in Table 2:

TABLE 2

| Comp. No. | Rate of application ppm | Nasturtium officinalis | Agrostis tenuis | Stellaria media | Digitaria sang. |
| --- | --- | --- | --- | --- | --- |
| 1.001 | 100 | 2 | 2 | 2 | 2 |
|  | 10 | 2 | 2 | 2 | 2 |
|  | 1 | 2 | 2 | 2 | 2 |
|  | 0.1 | 3 | 3 | 3 | 3 |
|  | 0.01 | 3 | 3 | 3 | 3 |
| 1.009 | 100 | 2 | 2 | 2 | 2 |
|  | 10 | 2 | 2 | 2 | 2 |
|  | 1 | 2 | 2 | 2 | 2 |
|  | 0.1 | 3 | 3 | 3 | 3 |
|  | 0.01 | 5 | 5 | 5 | 5 |
| 1.010 | 100 | 2 | 2 | 2 | 2 |
|  | 10 | 2 | 2 | 2 | 2 |
|  | 1 | 2 | 2 | 2 | 2 |
|  | 0.1 | 3 | 3 | 3 | 4 |
|  | 0.01 | 4 | 4 | 4 | 4 |
| 1.011 | 100 | 2 | 2 | 2 | 2 |
|  | 10 | 2 | 2 | 2 | 2 |
|  | 1 | 3 | 3 | 3 | 3 |
|  | 0.1 | 4 | 4 | 3 | 3 |
|  | 0.01 | 4 | 4 | 4 | 4 |
| 1.012 | 100 | 2 | 2 | 2 | 2 |
|  | 10 | 2 | 2 | 2 | 2 |
|  | 1 | 3 | 3 | 3 | 3 |
|  | 0.1 | 4 | 4 | 4 | 4 |
|  | 0.01 | 5 | 5 | 4 | 4 |

TABLE 2-continued

| Comp. No. | Rate of application ppm | Nasturtium officinalis | Agrostis tenuis | Stellaria media | Digitaria sang. |
|---|---|---|---|---|---|
| A | 100 | 2 | 2 | 1 | 2 |
|  | 10 | 2 | 2 | 2 | 2 |
|  | 1 | 4 | 6 | 2 | 3 |
|  | 0.1 | 9 | 9 | 7 | 7 |
|  | 0.01 | 9 | 9 | 9 | 9 |

A is ethyl 2-(5-isopropyl-5-methyl-4-oxo-4,5-dihydroimidazol-2-yl)-5-methylnicotinate known from published European patent application No. 41 623.

EXAMPLE 6

Herbicidal Action In Wild Rice (Paddy Rice)

The weeds *Echinocloa crus galli* and *Monocharia vag.*, which occur in water, are sown in plastic beakers (surface: 60 cm$^2$; volume: 500 ml). After sowing, the beakers are filled with water up to the surface of the soil. 3 days after sowing, the water level is increased to slightly above the soil surface (3-5 mm). Application is effected 3 days after sowing by spraying the beakers with an aqueous emulsion of the test compounds. The rate of application corresponds to a concentration of 4 kg of active ingredient per hectare (concentration of the spray mixture=550 l/ha). The beakers are then kept in the greenhouse under optimum growth conditions for rice weeds, i.e. at 25°-30° C. and at high humidity. The evaluation of the tests takes place 3 weeks after application.

Evaluation is made in accordance with the linear rating indicated in Example 3.

The test compounds of Table 1 exhibited good activity in this test.

EXAMPLE 7

Growth Inhibition of Tropical Leguminous Cover Crops

The test plants (*Centrosema plumieri* and *Centrosema pubescens*) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test, a marked reduction in new growth of the plants treated with compounds of Table 1 at concentrations of 50 to 3000 g/ha is observed (less than 20% of the new growth of untreated control plants), without damage being caused to the test plants.

EXAMPLE 8

Growth Regulation of Soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of formula I until thoroughly wetted. The concentration corresponds to up to 100 g a.i. per hectare. Evaluation is made about 5 weeks after application. Compared with untreated controls, the compounds of Table 1 of the invention markedly increase the number and weight of the harvested siliquae on the leading shoot.

EXAMPLE 9

Growth Inhibition of Cereals

Summer barley (*Hordeum vulgare*) and summer rye (*Secale*) are sown in sterilised soil in plastic beakers in a greenhouse and watered as required. The cereal shoots are treated about 21 days after sowing with an aqueous spray mixture of a compound of Table 1. The concentration corresponds to up to 100 g of active ingredient per hectare. Evaluation of the growth of the cereals is made 21 days after application. A comparison with untreated controls shows that the new growth of treated cereal plants is reduced (60-90% of the controls) and that the diameter of the stalks has in some cases increased.

EXAMPLE 10

Growth Inhibition of Grasses

Seeds of the grasses *Lolium perenne, Poa pratensis, Festuca ovina, Dactylis glomerate* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of Table 1. The concentration of test compound corrsponds to a rate of application of up to 500 g a.i. per hectare. The growth of the grasses is evaluated 21 days after application. The test compounds of formula I effect a reduction in new growth in the range of 10-30% in comparison with untreated controls.

EXAMPLE 11

Dessication and Defolation Action

Cotton plants of the Deltapine variety are reared in earthen-ware pots in a greenhouse. After the capsules have formed, the plants are sprayed with an aqueous formulation of compound No. 1 at rates of application corresponding to 1.2, 0.6 and 0.3 kg/ha in field application. Untreated plants act as controls. Evaluation of the test is made 3, 7 and 14 days after application of the active ingredient by determining the degree of defoliation (percentage of fallen leaves) and of desiccation (drying out of the leaves remaining on the plant).

In this test, plants treated with test compounds of Table 1 at rates of application 0.6 and 1.2 kg/ha are left after 7 days with only a few dried out leaves (<80% defoliation and dessication).

What is claimed is:

1. A heterocyclylalkyl ester of a 2-imidazolinonenicotinic acid of formula I

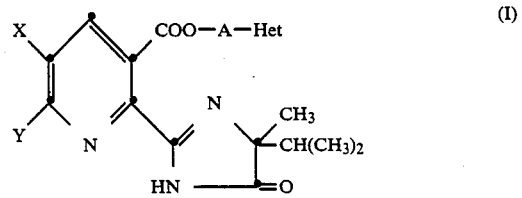

wherein

A is a straight chain or branched $C_1-C_4$alkylene bridge,

X and Y are each independently of the other hydrogen, $C_1-C_3$alkyl, $C_1-C_3$haloalkyl, $C_1-C_3$alkoxy, $C_1-C_3$haloalkoxy or halogen, or X and Y together form the butadiene bridge CH=CH—CH=CH, which may be substituted by halogen, cyano or $C_1-C_4$alkyl, and Het is a 5-membered heterocycle which contains one oxygen or sulfur atom and which may further contain one or two carbonyl groups, which heterocycle may also be substituted by halogen, formyl, $C_1-C_3$alkoxy, $C_1-C_3$haloalkoxy, nitro, amino, $C_1-C_3$ alkylamino or di($C_1-C_3$)alkylamino, with the proviso that Het may not be the unsubstituted furyl radical.

2. A compound according to claim 1, wherein
A is a methylene or ethylene bridge which is unsubstituted or substituted by methyl,
X is hydrogen or $C_1-C_3$alkyl,
Y is hydrogen and
Het is as defined in claim 1.

3. A compound according to claim 1, wherein
A is a methylene bridge,
X and Y are each independently of the other hydrogen, or $C_1-C_3$alkyl, and
Het is a tetrahydrofuranyl or furanyl ring which is unsubstituted or substituted by the formyl group.

4. A compound according to claim 3, wherein
A is a methylene bridge,
X is hydrogen or $C_1-C_3$alkyl,
Y is hydrogen and
Het is a tetrahydrofuranyl or furanyl ring, which is unsubstituted or substituted by the formyl group.

5. A compound according to claim 3, selected from tetrahydrofur-2-ylmethyl 2-(5-isopropyl-5-methyl-4-oxo-4,5-dihydro-imidazolin-2-yl)-5-methylnicotinate, furfuroyl-5-ylmethyl 2-(5-isopropyl-5-methyl-4-oxo-4,5-dihydro-imidazolin-2-yl)-5-ethyl-nicotinate and tetrahydrofur-2-ylmethyl 2-(5-isopropyl-5-methyl-4-oxo-4,5-dihydro-imidazolin-2-yl)-5-n-propylnicotinate.

6. A herbicidal and plant growth regulating composition which contains, as active ingredient, an effective amount of a heterocyclylalkyl ester of a 2-imidazolinonenicotinic acid according to claim 1, together with inert carriers and/or other adjuvants.

7. A method of selectively controlling weeds pre- or postemergence in crops of useful plants, which method comprises treating said useful plants or the crop areas thereof with an effective amount of a compound according to claim 1, or of a composition containing such a compound.

8. A method of inhibiting and suppressing plant growth beyond the 2-leaf stage, which method comprises treating the plants during their growth with an effective amount of a compound according to claim 1, or of a composition containing such a compound.

9. A method of dessicating and defoliating crops of cotton and potatoes to facilitate the harvesting thereof, which method comprises treating the crop, shortly before harvesting, with an effective amount of a compound according to claim 1, or of a composition containing such a compound.

* * * * *